(12) United States Patent
Berna Tejero et al.

(10) Patent No.: US 8,158,819 B2
(45) Date of Patent: Apr. 17, 2012

(54) PROCESS TO OBTAIN A HIGHLY SOLUBLE LINEAR ALKYLBENZENE SULFONATE

(75) Inventors: José Luis Berna Tejero, Boadilla del Monte (ES); José Luis Goncalvez De Almeida, Algeciras (ES); Ignacio López Serrano, La Linea de la Concepción (ES)

(73) Assignee: Cepsa Quimica S.A., Madrid (ES)

( * ) Notice: Subject to any disclaimer, the term of this patent is extended or adjusted under 35 U.S.C. 154(b) by 950 days.

(21) Appl. No.: 11/911,327

(22) PCT Filed: Apr. 12, 2005

(86) PCT No.: PCT/ES2005/000169
§ 371 (c)(1), (2), (4) Date: Jun. 11, 2008

(87) PCT Pub. No.: WO2006/108883
PCT Pub. Date: Oct. 19, 2006

(65) Prior Publication Data
US 2009/0221464 A1 Sep. 3, 2009

(51) Int. Cl.
*C07C 309/31* (2006.01)
(52) U.S. Cl. ............ 562/93; 562/94; 562/95; 562/96; 562/97
(58) Field of Classification Search ............ 562/93, 562/94, 95, 96, 97
See application file for complete search history.

(56) References Cited

U.S. PATENT DOCUMENTS

| 5,157,158 A | 10/1992 | Berna Tejero et al. |
| 6,133,217 A | 10/2000 | Lewis et al. |

FOREIGN PATENT DOCUMENTS

| JP | 2001-240588 | 9/2001 |
| JP | 2004-210709 | 7/2004 |
| WO | WO 00/40551 | 7/2000 |
| WO | WO 00/60041 | 10/2000 |
| WO | WO 01/05755 | 1/2001 |

OTHER PUBLICATIONS

Almeida et al. "Linear Alkylbenzene." *JAOCS*. vol. 71. No. 7. 1994 pp. 675-694.
Shah. "UOAP HF Alkylation Process." *Handbook of Petroleum Refining Process*. Robert A. Meyers Editor 1986. pp. 1-23.

*Primary Examiner* — Peter O Sullivan
(74) *Attorney, Agent, or Firm* — Merchant & Gould P.C.

(57) ABSTRACT

The present invention refers to a process to obtain a highly soluble linear alkylbenzene sulfonate (LAS). Specifically it comprises the addition, prior or after sulfonation of linear alkylbenzene and/or neutralization of linear alkylbenzene sulfonic acid of an hydrotropic composition. It also refers to a hydrotropic composition, to a highly soluble linear alkylbenzene sulfonate, to the use of the hydrotropic composition for making said linear alkylbenzene sulfonate highly soluble and to a cleaning composition comprising said linear alkylbenzene sulfonate.

17 Claims, 1 Drawing Sheet

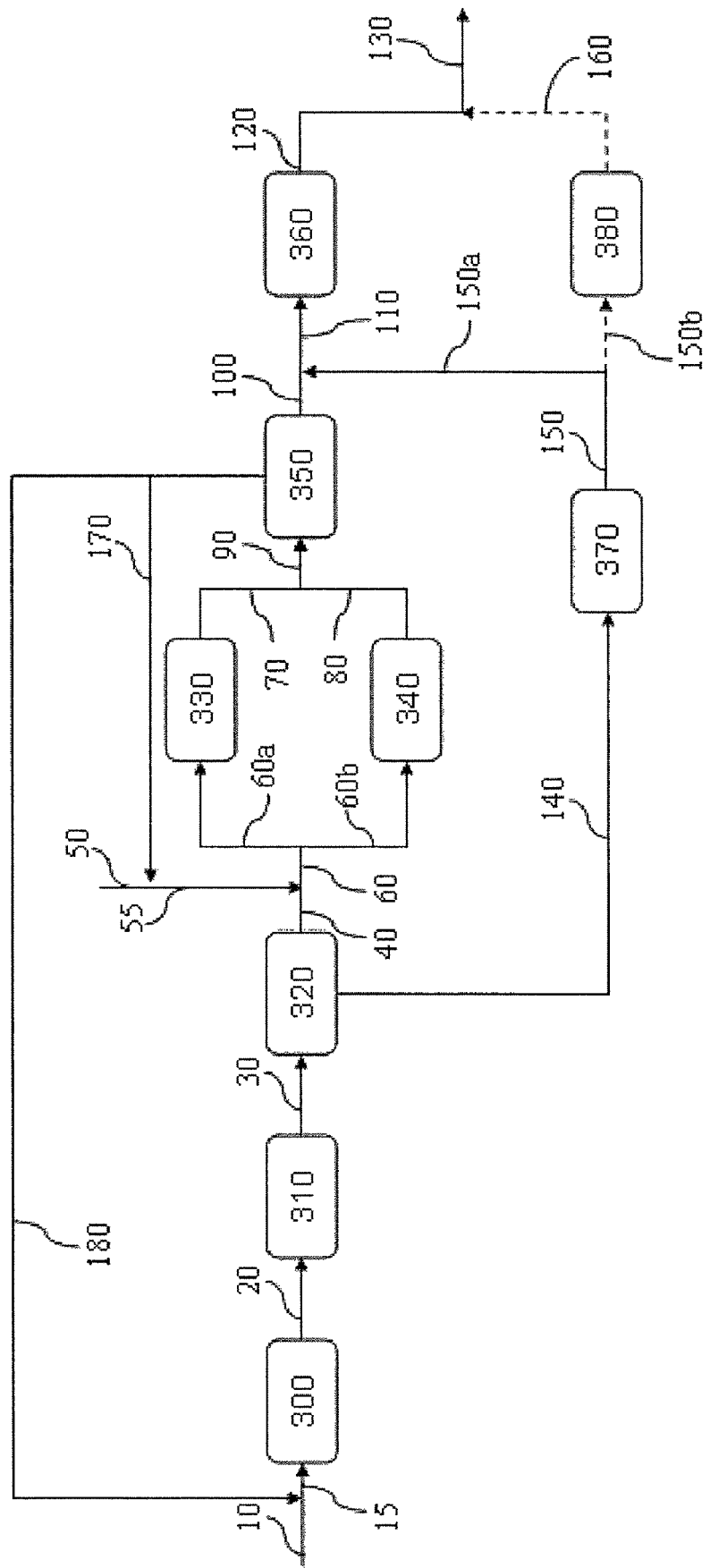

PROCESS TO OBTAIN A HIGHLY SOLUBLE LINEAR ALKYLBENZENE SULFONATE

FIELD OF THE INVENTION

The present invention refers to a process to obtain a highly soluble linear alkylbenzene sulfonate (LAS). Specifically it comprises the addition, prior or after sulfonation of linear alkylbenzene and/or neutralization of linear alkylbenzene sulfonic acid of an hydrotropic composition. It also refers to a hydrotropic composition, to a highly soluble linear alkylbenzene sulfonate, to the use of the hydrotropic composition for making said linear alkylbenzene sulfonate highly soluble and to a cleaning composition comprising said linear alkylbenzene sulfonate.

BACKGROUND OF THE INVENTION

Linear alkylbenzene sulfonate is the most commonly used anionic surfactant in cleaning compositions due to its excellent overall performance. For this reason, more than 3 million tons of LAS are consumed each year worldwide. LAS presents an outstanding cost/performance ratio, good stability over long periods of time and compatibility with a wide range of detergent components. Further, it shows a high degree of synergism in combination with some ingredients commonly used in cleaning formulations.

LAS is produced by sulfonation of Linear Alkylbenzene (LAB) and subsequent neutralization of the corresponding sulfonic acid (HLAS). Linear alkylbenzene is synthesized by the alkylation of benzene with linear olefins. Traditional processes for alkylation of aromatics compounds use Friedel-Craft type catalysts, for example, hydrofluoric acid, aluminum trichloride and the like. These processes are well known and used commercially, yielding a high conversion (>99% by weight) to LAB with selectivity to 2-phenyl-derivative relatively low, less than 30% by weight (P. R. Pujado, Handbook of Petroleum Refining Process, Robert A. Meyers (Editor), 1986, p. 1-23.)

Recent developments using various types of zeolytes, mordenites and other type of products as alkylation catalysts describe the production of LAB with a 2-phenyl-derivative content in the range of 30% to 80% by weight (J. L. Berna Tejero, A. Moreno Danvilla U.S. Pat. No. 5,157,158, 1992; and J. L. G. De Almeida, M. Dufaux, Y. Ben Taarit y C. Naccache, Journal od the American Oil Chemist's Society, Vo. 71, N°7, 675-694, 1994.).

LAB mixtures with external isomers content (2+3 phenyl) higher than 50% by weight are reported to provide after sulfonation and neutralization, a LAS with improved surface activity properties. These LAS however, show an important drawback caused by their low solubility in cold water conditions and high viscosity. In fact, LAS mixtures comprising more than 50% by weight of external isomers (2+3 phenyl) tend to form highly insoluble gels with high viscosity that makes them difficult to handle and process.

Earlier patent applications have attempted to improve the solubilization of LAS using different additives. Patent application WO 0040551 discloses the use of a commercial hydrotrope selected from the group of an alkylbenzene, an olefin, a methyl or ethyl ester of a carboxylic acid, an alkyl alcohol, non sulfonatable hydrotrope precursors, and mixtures thereof; either before or after sulfonation.

U.S. Pat. No. 6,133,217 discloses methods and compositions for the solubilization of linear alkylbenzene sulfonates in detergent formulations by the addition of one or more ethylene oxide/propylene oxide block copolymers.

Nevertheless, for LAS with very high concentrations of 2-phenyl-derivatives, none of the known hydrotropes seems to be suitable enough to sufficiently solubilize them and to reduce their viscosity. Moreover, the addition of hydrotrope precursors or hydrotropes increase the cost of the final cleaning composition formulations Accordingly, it would be desirable to find a hydrotrope with better performance to solubilize and reduce the viscosity of LAS with a high content of external isomers as well as improving the solubility and viscosity of those LAS with low content of external isomer. It would be preferably that such hydrotrope belongs to the family of alkylbenzenes and more preferably that it could be obtained in the facilities where linear alkylbenzenes are produced without significant capital investment.

DESCRIPTION OF THE INVENTION

It has now been found a process, as will be further detailed hereinafter, that can produce a highly soluble linear alkylbenzene sulfonate with a controlled 2-phenyl-derivative content. In view of the above, a first essential aspect of the present invention refers to a process to obtain a highly soluble linear alkylbenzene sulfonate, wherein at least 18% by weight of its isomers is the 2-phenyl-derivative, comprising the steps of:

i) obtaining an olefin/paraffin mixture through catalytic dehydrogenation of paraffins;

ii) purifying olefins from the mixture formed in step i);

iii) separating non linear compounds from the mixture obtained in step ii) by means of a selective adsorbent;

iv) treatment of the non linear compounds extracted in the step iii) to form the hydrotropic precursor;

v) alkylating benzene with the purified olefin/paraffin mixture obtained in step iii);

vi) purifying the crude linear alkylbenzenes obtained in step iv);

vii) sulfonating the linear alkylbenzenes obtained in the step vi);

viii) neutralizing the linear alkylbenzene sulfonic acids obtained in step vi);

Characterized in that said treatment of step iv) comprises at least one of the processes selected from the group consisting of fractionation, hydrogenation and/or selective adsorption, said hydrotropic precursor obtained in the step iv) being added to the purified linear alkylbenzene stream, either before the sulfonation and neutralization steps, the purified linear alkylbenzene stream and the hydrotropic precursor thus being sulfonated together, or the hydrotropic precursor being sulfonated and neutralized and subsequently added to the purified linear alkylbenzene sulfonate obtained after step viii).

In a preferred embodiment according to the present invention, said linear paraffin's of step i) comprises straight chain alkanes with 9 to 20 carbon atoms, preferably from 10 to 16 carbon atoms and more preferably from 10 to 14 carbon atoms. These paraffins can be dehydrogenated and purified by any process disclosed in the state of the art.

The non linear compounds formed in the dehydrogenation step are known for those skilled the art as undesirable by-products present in the LAB/LAS production process. However, according to the present invention it has now been found that they can be used as excellent hydrotropic precursors. Said non linear compounds are extracted using selective adsorbents, that work as molecular sieves, and subsequently treated in order to obtain the hydrotropic precursor stream. As mentioned above, this treatment includes steps such as fractionation, hydrogenation and/or selective adsorption.

In a preferred embodiment according to the present invention, the hydrotropic precursor stream comprises:
- from 2 to 20% by weight of alkyl aromatic compounds having one or more alkyl groups which have in total 4 carbon atoms;
- from 5 to 40% by weight of alkyl aromatic compounds having one or more alkyl groups which have in total 5 carbon atoms;
- from 15 to 30% by weight of alkyl aromatic compounds having one or more alkyl groups which have in total 6 carbon atoms;
- from 0.5 to 50% by weight of alkyl aromatic compounds having one or more alkyl groups which have in total 7 carbon atoms;
- from 0.01 to 10% by weight of alkyl aromatic compounds having one or more alkyl groups which have in total 8 carbon atoms;
- from 0.5 to 10% by weight of alkyl aromatic compounds having one or more alkyl groups which have in total 9 carbon atoms; and
- from 0.5 to 10% by weight of alkyl aromatic compounds having one or more alkyl groups which have in total 10 carbon atoms.

The 2-phenyl-derivative content above mentioned, is defined as the weight percent of the 2-phenyl-derivative in an LAB or LAS mixture, and is calculated with the following formula:

$$\text{2-phenyl-derivative}[\%] = (\text{mass of 2-phenyl-derivative}) \times 100 / (\text{total mass of LAB or LAS})$$

Preferably, two different alkylation reactors are used simultaneously in the present invention: the first one uses an alkylation catalyst which produces a crude linear alkylbenzene with a 2-phenyl-derivative content of 20% by weight maximum, preferably between 15 and 20%. The catalysts that can be used are already known in the state of the art and comprises, for example, hydrofluoric acid, aluminum trichloride, zeolyte Y and the like. The design of the reactor could be a continuous stirring tank reactor, a fixed bed reactor or a fluidized bed reactor. The fixed bed reactor design is preferred.

The second alkylation reactor uses an alkylation catalyst which produce a crude linear alkylbenzene with a 2-phenyl-derivative content of at least 20% by weight. The catalysts to be used comprises among others zeolytes, mordenites and the like. The design of the reactor could be slurry reactor, fixed bed reactor or fluidized bed reactor. For this type of process, mainly solid catalyst and fixed bed reactors are preferred.

It's preferred that the linear alkylbenzene with a controlled 2-phenyl-derivative content and the hydrotropic precursor are sulfonated and subsequently neutralized together. The composition of the mixture on a weight basis (linear alkylbenzene with a controlled 2-phenyl-derivative content and the hydrotropic precursor) being 80:20, preferably 85:15 and more preferably between 90:10 95:05 respectively.

A second aspect according to the present invention refers to a hydrotropic precursor characterised in that it comprises:
- from 2 to 20% by weight of alkyl aromatic compounds having one or more alkyl groups which have in total 4 carbon atoms;
- from 5 to 40% by weight of alkyl aromatic compounds having one or more alkyl groups which have in total 5 carbon atoms;
- from 15 to 30% by weight of alkyl aromatic compounds having one or more alkyl groups which have in total 6 carbon atoms;
- from 0.5 to 50% by weight of alkyl aromatic compounds having one or more alkyl groups which have in total 7 carbon atoms;
- from 0.01 to 10% by weight of alkyl aromatic compounds having one or more alkyl groups which have in total 8 carbon atoms;
- from 0.5 to 10% by weight of alkyl aromatic compounds having one or more alkyl groups which have in total 9 carbon atoms; and
- from 0.5 to 10% by weight of alkyl aromatic compounds having one or more alkyl groups which have in total 10 carbon atoms.

Preferably, said hydrotropic precursor is obtainable from a procedure of catalityc dehydrogention of paraffins.

Another aspect according to the present invention refers to a Linear alkylbenzene composition comprising:
a) from 80 to 95% by weight of a linear alkylbenzene, wherein at least 18% by weight of its isomers is the 2-phenyl-derivative and wherein the alkyl chain has between 9 and 20 carbon atoms, preferably from 10 to 16 carbon atoms and more preferably from 10 to 14 carbon atoms;
b) from 5 to 20% by weight of said hydrotropic precursor.

Further, another aspect according to the present invention refers to highly soluble linear alkylbenzene sulfonate, comprising:
a) from 80 to 95% by weight of a linear alkylbenzene sulfonate, wherein at least 18% by weight of its isomers is the 2-phenyl-derivative and wherein the alkyl chain has between 9 and 20 carbon atoms, preferably from 10 to 16 carbon atoms and more preferably from 10 to 14 carbon atoms;
b) from 5 to 20% by weight of a hydrotropic composition comprising:
- from 2 to 20% by weight of sulfonated alkyl aromatic compounds having one or more alkyl groups which have in total 4 carbon atoms;
- from 5 to 40% by weight of sulfonated alkyl aromatic compounds having one or more alkyl groups which have in total 5 carbon atoms;
- from 15 to 30% by weight of sulfonated alkyl aromatic compounds having one or more alkyl groups which have in total 6 carbon atoms;
- from 0.5 to 50% by weight of sulfonated alkyl aromatic compounds having one or more alkyl groups which have in total 7 carbon atoms;
- from 0.01 to 10% by weight of sulfonated alkyl aromatic compounds having one or more alkyl groups which have in total 8 carbon atoms;
- from 0.5 to 10% by weight of sulfonated alkyl aromatic compounds having one or more alkyl groups which have in total 9 carbon atoms; and
- from 0.5 to 10% by weight of sulfonated alkyl aromatic compounds having one or more alkyl groups which have in total 10 carbon atoms.

A further aspect according to the present invention refers to cleaning compositions suitable for hand dishwashing preparations, hard surface cleaners, liquid laundry products, laundry products in powder, cleaning preparations in paste form, gels and laundry bars, comprising a) a soluble linear alkylbenzene sulfonate surfactant according to claim 10 in concentrations between 1 wt % and 99 wt %, b) between 99 wt % and 1 wt % of other commonly used detergent ingredients selected from the group formed by fatty alcohol derivatives, co-surfactants, builders, solvents, additives and mixtures thereof.

Another aspect according to the present invention refers to the use of said hydrotropic precursor, after its sulfonation and neutralization, to improve the solubilization of linear alkylbenzene sulfonates.

The solubility of LAS in water at high concentration may be estimated by the "cooled cloud point". The cooled cloud point (CCP) is the temperature corresponding to permanent cloudiness when the temperature is decreased. This parameter is applicable to anionic surfactants and formulations and it is an important variable to take into account in detergent formulation development. It should be as low as possible to avoid cloudiness of a finished product due to changes in temperature.

FIG. 1 represents a non-limiting scheme for the practice of this invention.

Stream 15 is the paraffin feed to the dehydrogenation unit and it comprises the mixture of fresh paraffins stream 10 and those unconverted recycled paraffins via stream 180 from the crude alkylbenzene purification unit 350. The dehydrogenation unit 300 converts partially the feed of paraffins to a mixture of mono-olefins mainly.

The olefins purification unit 310 is fed with the effluent of the dehydrogenation unit via stream 20 increasing the yield to mono-olefins after converting some of the by-products generated in the dehydrogenation unit. Stream 30 is processed in unit 320, which contains a selective adsorbent in order to remove the non-linear compounds produced in the process.

Fresh benzene is pumped to the process via stream 50, and mixed with recycled unreacted benzene (stream 170) that came from the crude alkylbenzene purification unit 350. The mixture of these two streams form the benzene feed (stream 55) which is mixed with the effluent (stream 40) of the selective adsorption unit 320 to form the stream 60 which is the fed to the alkylation units.

Stream 60 is divided in two identical streams, 60a and 60b, that fed two distinct alkylation reactors 330 an 340 respectively; alkylation reactor 330 uses a catalyst that produce a crude linear alkylbenzene (stream 70) with a maximum content of 2-phenyl-derivative of 20%, while alkylation reactor 340 uses a catalyst that produce a crude linear alkylbenzene (stream 80) with a 2-phenyl-derivative content of at least 20% by weight. Streams 70 and 80 are mixed in different proportions in order to obtain a crude linear alkylbenzene (stream 90) with a controlled 2-phenyl-derivative content.

Stream 90 is fed to the crude alkylbenzene purification unit 350 where unreacted benzene, paraffins and by-products heavier than linear alkylbenzene are distilled in order to obtain a linear alkylbenzene (stream 100) of high purity.

The non-linear compounds extracted in unit 320 are pumped to the specific treatment unit 370 via stream 140. This unit comprises steps such as fractionation, hydrogenation and or selective adsorption treatment in order to obtain the hydrotropic precursor (stream 150).

Depending on the operating conditions of the process of this invention, stream 150 could be routed to stream 150a or 150b, so the high purity linear alkylbenzene stream 100 and the hydrotrope precursor stream 150a are mixed forming the stream 110 and sulfonated/neutralized together in unit 360 or sulfonated/neutralized separately: (stream 100 in unit 360 and stream 150b in unit 380). They are then mixed forming the stream 130 which comprises a highly soluble linear alkylbenzene sulfonate with a controlled 2-phenyl-derivative content.

The invention is further described, only for illustrative means, through the following examples, which should never be considered to limit the scope of the present invention.

EXAMPLES

Several experiences where carried out to measure the cooled cloud point and viscosity of different mixtures of LAS containing different hydrotropic compositions, including that specified in the present invention. Representative results are shown through the following experiments.

TABLE 1

LAB detailed composition

| | LAB types | | | | |
|---|---|---|---|---|---|
| | A | B | C (wt %) | D | E |
| Homologue distribution | | | | | |
| <Phenyl C10 | 0.8 | — | 0.4 | 0.5 | — |
| Phenyl C10 | 11.6 | 15.2 | 28.4 | 10.4 | 14.3 |
| Phenyl C11 | 29.2 | 33.6 | 50.0 | 30.4 | 33.8 |
| Phenyl C12 | 36.8 | 32.1 | 20.6 | 30.2 | 31.6 |
| Phenyl C13 | 21.4 | 18.4 | 0.6 | 26.6 | 19.7 |
| Phenyl C14 | 0.2 | 0.7 | 0.0 | 1.8 | 0.6 |
| Average Molecular weight | 240.8 | 239.0 | 230.9 | 242.2 | 239.8 |
| Isomer Distribution | | | | | |
| 2-Phenyl alkanes | 15.5 | 68.3 | 71.0 | 27.4 | 55.3 |
| 3-Phenyl alkanes | — | 17.1 | 15.6 | — | 17.4 |
| 4-Phenyl alkanes | — | 2.1 | 1.9 | — | 6.8 |
| 5-Phenyl alkanes | — | 1.0 | 1.1 | — | 6.5 |
| 6-Phenyl alkanes | — | 0.5 | 0.5 | — | 3.8 |

The composition of the hydrotropic precursor obtained from the special treatment is described in the following table:

TABLE 2

Hydrotropic precursor average composition

| Carbon Chain Distribution | [% wt] |
|---|---|
| Phenyl C4 | 5-10 |
| Phenyl C5 | 15-25 |
| Phenyl C6 | 20-30 |
| Phenyl C7 | 10-20 |
| Phenyl C8 | 5-15 |
| Phenyl C9 | 5-15 |
| Phenyl C10 | 5-15 |
| Total alkyl aromatic compounds | 80-95 |
| Other compounds | 5-10 |
| Average Molecular weight | 160-170 |

Several sulfonations were carried out with the LAB and LAB/hydrotropic precursor mixture using $SO_3$ diluted in dry air as sulfonating agent. The average sulfonation conditions used were:

TABLE 3

Sulfonation conditions

| $SO_3$/LAB mol ratio | 1.10:1 |
|---|---|
| Reaction time | 1.5 hours |
| Reaction temperature | 40-45° C. |
| Digesting time | 1 hour |
| Digesting temperature | 40-45° C. |
| Hydrolisis time | 0.5 hour |
| Hydrolisis temperature | 40-45° C. |

The sulfonic acids of the LAB and LAB/hydrotropic precursor mixture were neutralized with caustic soda at 10% by weight to obtain the corresponding final LAS and LAS/hydrotropic composition (sodium salt), with an active matter content around 50% by weight. Using this solution, different cleaning compositions were prepared in order to evaluate the effect of the hydrotope precursor as well as other industrial hydrotropes on physical chemical properties such as solubility and viscosity.

Example 1

An LAB (type A) was sulfonated/neutralized as described above. A mixture (90:10) of LAB type A and hydrotrope precursor was also sulfonated/neutralized. The results of the solubility test, expressed as cloud point are presented in Table 4.

TABLE 4

Cloud point of LAS type A

| | Active Matter in Cleaning composition [% wt] | | |
|---|---|---|---|
| Cloud Point [° C.] | 20% | 25% | 30% |
| 100% A | 7 | 17 | (*) |
| 90% A + 10% SXS (Sodium xylene sulfonate) | 8 | 15 | 20 |
| 90% A + 10% Hydrotrope Precursor | 1 | 8 | 16 |

(*) Cloudy at room temperature

Example 2

The results of the viscosity test on the same mixtures of the example 1 are shown in Table 5.

TABLE 5

Viscosity of LAS type A at 25° C.

| | Active Matter in Cleaning composition [% wt] | | |
|---|---|---|---|
| Dynamic viscosity [cP] | 20% | 25% | 30% |
| 100% A | 750 | 2000 | 2250 |
| 90% A + 10% SXS | 250 | 1100 | 1550 |
| 90% A + 10% Hydrotrope Precursor | 20 | 150 | 650 |

Example 3

An LAB (type B) was sulfonated/neutralized as described above. A mixture (90:10) of LAB type B and hydrotrope precursor was also sulfonated/neutralized. The results of the solubility test, expressed as cloud point are presented in Table 6.

TABLE 6

Cloud point of LAS type B

| | Active Matter in Cleaning composition [% wt] | | |
|---|---|---|---|
| Cloud Point [° C.] | 20% | 25% | 30% |
| 100% B | 14 | 17 | (*) |
| 90% B + 10% SXS | 17 | 20 | (*) |
| 90% B + 10% Hydrotrope Precursor | 13 | 16 | 20 |

(*) Cloudy at room temperature

Example 4

The results of the viscosity test on the same mixtures of the example 3 are shown in Table 7.

TABLE 7

Viscosity of LAS type B at 25° C.

| | Active Matter in Cleaning composition [% wt] | | |
|---|---|---|---|
| Dynamic viscosity [cP] | 20% | 25% | 30% |
| 100% B | 500 | 5000 | (+) |
| 90% B + 10% SXS | 25 | 175 | 470 |
| 90% B + 10% Hydrotrope Precursor | 5 | 12 | 70 |

(+) Pseudoplastic behaviour

Example 5

An LAB (type C) was sulfonated/neutralized as described above A mixture (90:10) of LAB type C and hydrotrope precursor was also sulfonated/neutralized. The results of the solubility test, expressed as cloud point are shown in Table 8.

TABLE 8

Cloud point of LAS type C

| | Active Matter in Cleaning composition [% wt] | | |
|---|---|---|---|
| Cloud Point [° C.] | 20% | 25% | 30% |
| 100% C | 16 | 20 | 24 |
| 90% C + 10% SXS | 12 | 15 | 17 |
| 90% C + 10% Hydrotrope Precursor | 7 | 9 | 13 |

Example 6

The results of the viscosity test over the same mixtures of the example 5 are shown in Table 9

TABLE 9

Viscosity of LAS type C

| | Active Matter in Cleaning composition [% wt] | | |
|---|---|---|---|
| Dynamic viscosity [cP] | 20% | 25% | 30% |
| 100% C | 75 | 1250 | (+) |

(+) Pseudoplastic behaviour

Example 7

TABLE 10

Cloud point of LAS type D

| | Active Matter in Cleaning composition [% wt] | | |
|---|---|---|---|
| | 20% | 25% | 30% |
| | Cloud Point [° C.] | | |
| 100% D | 0 | 4 | 13 |
| 90% D + 10% SXS | 1 | 6 | 11 |

Example 8

TABLE 11

Viscosity of LAS type D at 25° C.

| | Active Matter in Cleaning composition [% wt] | | |
|---|---|---|---|
| | 20% | 25% | 30% |
| | Dynamic viscosity [cP] | | |
| 100% D | 400 | 2700 | 4200 |
| 90% D + 10% SXS | 250 | 1100 | 1550 |

The invention claimed is:

1. Process to obtain a highly soluble linear alkylbenzene sulfonate, wherein at least 18% by weight of isomers of said highly soluble linear alkylbenzene sulfonate are the 2-phenyl derivatives, comprising the steps of:
   i) obtaining an olefin/paraffin mixture through catalytic dehydrogenation of paraffins;
   ii) purifying olefins from the mixture formed in step i);
   iii) separating non linear compounds from the mixture obtained in step ii) by means of a selective adsorbent;
   iv) treatment of the non linear compounds extracted in the step iii) to form the hydrotropic precursor;
   v) alkylating benzene with the purified olefin/paraffin mixture obtained in step iii);
   vi) purifying the crude linear alkylbenzenes obtained in step v);
   vii) sulfonating the linear alkylbenzenes obtained in the step vi);
   viii) neutralizing the linear alkylbenzene sulfonic acids obtained in step vi);
wherein said treatment of step iv) comprises at least one of the processes selected from the group consisting of fractionation, hydrogenation and/or selective adsorption, said hydrotropic precursor obtained in the step iv) being added to the purified linear alkylbenzene stream, either before the sulfonation and neutralization steps, the purified linear alkylbenzene stream and the hydrotropic precursor thus being sulfonated together, or the hydrotropic precursor being sulfonated and neutralized and subsequently added to the purified linear alkylbenzene sulfonate obtained after step viii).

2. The process according to claim 1 wherein the paraffins used have from 9 to 20 carbon atoms.

3. Process according to claim 1, wherein the alkylation of step v) of said benzene with said olefin/paraffin mixture obtained in step iii) comprises two parallel alkylation processes, selected from:
   v.1) an alkylation process with a catalyst to produce a crude linear alkylbenzene with a maximum 2-phenyl-derivative content of 20% by weight; and
   v.2) an alkylation process with a catalyst to produce a crude linear alkylbenzene with a minimum 2-phenyl-derivative content of 20% by weight.

4. Process according to claim 3, wherein the crude linear alkylbenzenes of steps v.1) and v.2) are mixed in variable proportions.

5. Process according to claim 1, wherein said hydrotropic precursor comprises:
   from 2 to 20% by weight of alkyl aromatic compounds having one or more alkyl groups which have in total 4 carbon atoms;
   from 5 to 40% by weight of alkyl aromatic compounds having one or more alkyl groups which have in total 5 carbon atoms;
   from 15 to 30% by weight of alkyl aromatic compounds having one or more alkyl groups which have in total 6 carbon atoms;
   from 0.5 to 50% by weight of alkyl aromatic compounds having one or more alkyl groups which have in total 7 carbon atoms;
   from 0.1 to 10% by weight of alkyl aromatic compounds having one or more alkyl groups which have in total 8 carbon atoms;
   from 0.5 to 10% by weight of alkyl aromatic compounds having one or more alkyl groups which have in total 9 carbon atoms; and
   from 0.5 to 10% by weight of alkyl aromatic compounds having one or more alkyl groups which have in total 10 carbon atoms.

6. A hydrotropic precursor comprising:
   from 2 to 20% by weight of alkyl aromatic compounds having one or more alkyl groups which have in total 4 carbon atoms;
   from 5 to 40% by weight of alkyl aromatic compounds having one or more alkyl groups which have in total 5 carbon atoms;
   from 15 to 30% by weight of alkyl aromatic compounds having one or more alkyl groups which have in total 6 carbon atoms;
   from 0.5 to 50% by weight of alkyl aromatic compounds having one or more alkyl groups which have in total 7 carbon atoms;
   from 0.01 to 10% by weight of alkyl aromatic compounds having one or more alkyl groups which have in total 8 carbon atoms;
   from 0.5 to 10% by weight of alkyl aromatic compounds having one or more alkyl groups which have in total 9 carbon atoms; and
   from 0.5 to 10% by weight of alkyl aromatic compounds having one or more alkyl groups which have in total 10 carbon atoms.

7. A hydrotropic precursor according to claim 6, obtainable from a procedure of catalytic dehydrogenation of paraffins.

8. Linear alkylbenzene composition comprising:
   a) from 80 to 95% by weight of a linear alkylbenzene, wherein at least 18% by weight of isomers present in said linear alkylbenzene are the 2-phenyl-derivatives and wherein the alkyl chain has between 9 and 20 carbon atoms;
   b) from 5 to 20% by weight of a hydrotropic precursor according to claim 6.

9. Highly soluble linear alkylbenzene sulfonate, comprising:
  a) from 80 to 95% by weight of a linear alkylbenzene sulfonate, wherein at least 18% by weight of said linear alkylbenzene sulfonate isomers are the 2-phenyl derivatives and wherein the alkyl chain has between 9 and 20 carbon atoms;
  b) from 5 to 20% by weight of a hydrotropic composition comprising:
    from 2 to 20% by weight of sulfonated alkyl aromatic compounds having one or more alkyl groups which have in total 4 carbon atoms;
    from 5 to 40% by weight of sulfonated alkyl aromatic compounds having one or more alkyl groups which have in total 5 carbon atoms;
    from 15 to 30% by weight of sulfonated alkyl aromatic compounds having one or more alkyl groups which have in total 6 carbon atoms;
    from 0.5 to 50% by weight of sulfonated alkyl aromatic compounds having one or more alkyl groups which have in total 7 carbon atoms;
    from 0.1 to 10% by weight of sulfonated alkyl aromatic compounds having one or more alkyl groups which have in total 8 carbon atoms;
    from 0.5 to 10% by weight of sulfonated alkyl aromatic compounds having one or more alkyl groups which have in total 9 carbon atoms; and
    from 0.5 to 10% by weight of sulfonated alkyl aromatic compounds having one or more alkyl groups which have in total 10 carbon atoms.

10. Cleaning compositions suitable for hand dishwashing preparations, hard surface cleaners, liquid laundry products, laundry products in powder, cleaning preparations in paste form, gels and laundry bars, comprising a) a soluble linear alkylbenzene sulfonate surfactant according to claim 9 in concentrations between 1 wt % and 99 wt %, b) between 99 wt % and 1 wt % of other commonly used detergent ingredients selected from the group formed by fatty alcohol derivatives, co-surfactants, builders, solvents, additives and mixtures thereof.

11. The process according to claim 2, wherein the paraffins used have from 10 to 16 carbon atoms.

12. The process according to claim 11, wherein the paraffins used have from 10 to 14 carbon atoms.

13. The linear alkylbenzene composition according to claim 8, wherein said alkyl chain has from 10 to 16 carbon atoms.

14. The linear alkylbenzene composition according to claim 13, wherein said alkyl chain has from 10 to 14 carbon atoms.

15. The highly soluble linear alkylbenzene sulfonate according to claim 9, wherein said alkyl chain has from 10 to 16 carbon atoms.

16. The highly soluble linear alkylbenzene sulfonate according to claim 15, wherein said alkyl chain has from 10 to 14 carbon atoms.

17. A method for using a hydrotropic precursor comprising
  from 2 to 20% by weight of alkyl aromatic compounds having one or more alkyl groups which have in total 4 carbon atoms;
  from 5 to 40% by weight of alkyl aromatic compounds having one or more alkyl groups which have in total 5 carbon atoms;
  from 15 to 30% by weight of alkyl aromatic compounds having one or more alkyl groups which have in total 6 carbon atoms;
  from 0.5 to 50% by weight of alkyl aromatic compounds having one or more alkyl groups which have in total 7 carbon atoms;
  from 0.1 to 10% by weight of alkyl aromatic compounds having one or more alkyl groups which have in total 8 carbon atoms;
  from 0.5 to 10% by weight of alkyl aromatic compounds having one or more alkyl groups which have in total 9 carbon atoms; and
  from 0.5 to 10% by weight of alkyl aromatic compounds having one or more alkyl groups which have in total 10 carbon atoms,
sulfonated and neutralized, able to improve the solubilisation of linear alkylbenzene sulfonates;
  said method comprising adding said hydrotropic precursor to a stream of said purified linear alkylbenzene sulfonates.

* * * * *